(12) United States Patent
Zhang et al.

(10) Patent No.: US 7,351,954 B2
(45) Date of Patent: Apr. 1, 2008

(54) METHOD AND APPARATUS FOR DETECTING GAS CONCENTRATION WITH INFRARED ABSORPTION CHARACTERISTICS

(75) Inventors: Wei Zhang, Nanshan (CN); Huiling Zhou, Nanshan (CN); Zhigang Wu, Nanshan (CN)

(73) Assignee: Shenzhen Mindray Bio-Medical Electronics Co., Ltd., Shenzhen (CN)

( * ) Notice: Subject to any disclaimer, the term of this patent is extended or adjusted under 35 U.S.C. 154(b) by 297 days.

(21) Appl. No.: 11/312,702

(22) Filed: Dec. 20, 2005

(65) Prior Publication Data

US 2007/0034792 A1 Feb. 15, 2007

(30) Foreign Application Priority Data

Aug. 12, 2005 (CN) ........................ 2005 1 0036628

(51) Int. Cl.
*G01D 18/00* (2006.01)
*G12B 13/00* (2006.01)

(52) U.S. Cl. .................................................. 250/252.1

(58) Field of Classification Search ............. 250/252.1, 250/339.09, 339.12, 339.07, 339.06, 339.01, 250/341.1, 341.5, 343

See application file for complete search history.

(56) References Cited

U.S. PATENT DOCUMENTS

| | | | | |
|---|---|---|---|---|
| 4,004,146 | A | * | 1/1977 | Blunck ........................ 250/345 |
| 4,188,534 | A | * | 2/1980 | Watanabe et al. ............ 250/345 |
| 5,003,175 | A | * | 3/1991 | Fabinski et al. ............. 250/345 |
| 5,077,469 | A | * | 12/1991 | Fabinski et al. ............. 250/345 |
| 5,206,511 | A | * | 4/1993 | Apperson et al. ........... 250/343 |

(Continued)

FOREIGN PATENT DOCUMENTS

CN 2290850 9/1998

(Continued)

*Primary Examiner*—David P. Porta
*Assistant Examiner*—David S Baker
(74) *Attorney, Agent, or Firm*—Workman Nydegger

(57) ABSTRACT

A method and an apparatus for detecting gas concentration with infrared absorption characteristics have the function of automatic calibration. The function of automatic calibration is accomplished in such a manner that a reference chamber filled with $CO_2$ gas of a known concentration is added in the apparatus; by switching the reference chamber in real-time or periodically into the detecting light path, the measured value of the concentration of $CO_2$ gas in the reference chamber can be obtained; then by comparing the measured value with the standard value of known concentration of $CO_2$ gas, the calibration factor is obtained; once finishing the calibration process, a detecting chamber is switched into the detecting light path so that a concentration of a gas can be detected accurately. In the apparatus of the present invention, the same detecting light path (e.g. the infrared light source, and the light filter, etc.), the same infrared light signal processing unit (e.g. the infrared sensor, the amplification circuit and the single-chip microcomputer system, etc.) are used for both the calibration process and the detection process. Therefore, the negative effect caused by difference of the characteristics of temperature drift of circuit components between different light paths in prior art can be eliminated, and the errors in the detected results by using the apparatus in the present invention is greatly reduced. In addition, the structure of the apparatus in the present invention is relatively simple, resulting in the lower production cost and no necessity for the manual maintenance.

19 Claims, 1 Drawing Sheet

U.S. PATENT DOCUMENTS

| | | | |
|---|---|---|---|
| 5,677,534 A * | 10/1997 | Araya | 250/345 |
| 5,764,354 A * | 6/1998 | Aidam et al. | 356/243.1 |
| 5,793,044 A * | 8/1998 | Mace et al. | 250/343 |
| 5,965,887 A * | 10/1999 | Patton | 250/339.09 |
| 6,201,645 B1 | 3/2001 | Ohuchi | |
| 6,274,870 B1 * | 8/2001 | Kubo et al. | 250/339.13 |
| 6,313,464 B1 | 11/2001 | Schrader | |
| 6,320,192 B1 * | 11/2001 | Tominaga et al. | 250/344 |
| 2003/0230716 A1 * | 12/2003 | Russell et al. | 250/339.13 |

FOREIGN PATENT DOCUMENTS

| | | |
|---|---|---|
| CN | 1482449 | 3/2004 |
| JP | A-S60-31043 | 2/1985 |
| JP | A-2001-27601 | 1/2001 |
| JP | A-2002-350340 | 12/2002 |

* cited by examiner

METHOD AND APPARATUS FOR DETECTING GAS CONCENTRATION WITH INFRARED ABSORPTION CHARACTERISTICS

FIELD OF THE INVENTION

The present invention relates to a technique for detecting or analyzing materials with optical means, and more particularly to a method and an apparatus for detecting gas concentration with infrared absorption characteristics, which has the function of automatic calibration and are more preferably used to detect the concentration of $CO_2$ gas contained in the breathing gas from human being in medical application.

BACKGROUND OF THE INVENTION

At present, the principle of detecting a gas concentration is generally based on non-dispersive infrared (NDIR) technique, i.e. an infrared light with a specific waveband is selected and allowed to pass through a sample gas according to the absorption characteristics of the sample gas to this infrared light, the relationship between the attenuated intensity of the infrared light and the concentration of the sample gas to be detected follows the Beer-Lambert law. For instance, as to an apparatus for detecting concentration of $CO_2$ in the breathing gas, since an obvious absorption peak of $CO_2$ molecule occurs as the wavelength of the infrared light is 4.26 micrometer, the concentration of $CO_2$ gas can be calculated in terms of the attenuated intensity of the infrared light with the wavelength of about 4.26 micrometer. In order to compute the concentration of $CO_2$ gas, $CO_2$ gas with known concentration is input into the apparatus, and the corresponding intensity of the infrared light is detected and recorded so that an intensity-concentration curve can be obtained. Later, the concentration of $CO_2$ contained in a gas to be detected can be determined by means of the reference intensity-concentration curve according to the detected intensity of infrared light. Owing to the differences in a light resource, a detector (i.e. sensor), a circuit for each detecting apparatus, the corresponding calibrating factor must be preset before shipping out of the factory. By inputting $CO_2$ gas with known standard concentration into the apparatus and comparing the difference between the detected concentration and the standard concentration, the calibrating factor is determined and used for correcting the measured results of the concentration. However, the detected results by the apparatus may be not accurate due to the ageing problem of the light source, the detector, etc. after long time service. Therefore, the periodical maintenance is required every half year or one year. That is, the calibration process should be implemented again by inputting $CO_2$ gas having a standard concentration. This calibration process is complex and inconvenient because some equipment, such as a gas cylinder filled with $CO_2$ gas having a standard concentration, gas pressure regulator, pipes and so on, need to be prepared.

In order to maintain the accuracy of the detected results during its long period of service time, dual beam mode is usually employed. With two light paths being generated by a beam splitter in the apparatus, one light path passes through the gas to be detected, and the other one as a reference light path passes through a sealed reference gas. The concentration of the sealed reference gas in the reference light path is known and thereby used as a reference concentration, so that automatic calibration process can be realized, for example in U.S. Pat. Nos. 5,764,354 and 5,077,469. However, in the detecting apparatus with dual beam mode, the intensities of two light beams are measured by two detectors respectively. Since the aging extents of two detectors are different after long time service and the difference between two detectors themselves always exist, the error in the detected results may exist during the detection process.

Therefore, those apparatuses for detecting the concentration of $CO_2$ with the absorption characteristics of infrared light in the prior art have the following disadvantages:

1. Because the apparatus need to be calibrated periodically and calibration process is complex, cost of maintenance for the apparatus is high.

2. For dual beam mode, two detectors are used to detect light intensities in two light paths. But, since the aging extents of two detectors are different after long time service and the difference between two detectors themselves always exist, the accuracy of the detected results may be deteriorated.

SUMMARY OF THE INVENTION

An object of the present invention is to provide a method and an apparatus for detecting gas concentration with infrared absorption characteristics, which has the function of automatic calibration and stability of the detection accuracy, in order to overcome the disadvantages in prior art.

In one aspect of the present invention, there is a method for detecting gas concentration with infrared absorption characteristics, comprising the following steps:

a. feeding gas containing a certain amount of gas to be detected into a detecting chamber in a detecting light path;

b. transmitting an infrared light containing a specific wavelength $\lambda$ through the detecting chamber, so as to generate an infrared light signal reflecting concentration information of the gas to be detected, wherein the gas to be detected has maximum absorption to the infrared light at the specific wavelength $\lambda$;

c. processing the infrared light signal which passed through the detecting chamber, so as to obtain a measured value $C_0$ of the concentration of the gas to be detected; and d. computing a calibrated value C of the concentration of the gas to be detected according to a formula $C=C_0*\beta$, wherein $\beta$ is a calibration factor;

wherein the calibration factor $\beta$ is obtained by a calibration step of:

switching a reference chamber filled with a reference gas having a known concentration value $C_1$ into the detecting light path to replace the detecting chamber, then repeating the step b and the step c to obtain a measured value $C_2$ of the concentration of the reference gas in the reference chamber, and thus determining the calibration factor $\beta$ by a formula of $\beta=C_1/C_2$ according to the measured value $C_2$ and the known concentration value $C_1$ of the reference gas.

According to the above-mentioned method, the step b further comprises a step of converting the infrared light into an infrared light pulse, wherein the infrared light pulse passes through the detecting chamber, and thereby forms an infrared light pulse signal reflecting concentration information of the gas to be detected.

According to the above-mentioned method, said processing in the step c comprises the steps of:

c1: transmitting the infrared light pulse signal which has passed through the detecting chamber into a band pass filter having a central wavelength as the specific wavelength $\lambda$, and then converting the infrared light pulse signal which has passed through the band pass filter into an electrical signal;

c2: amplifying the electrical signal and then sending the amplified electrical signal to a microcomputer system; and c3. computing a measured value $C_0$ of the concentration of the gas to be detected in the detecting chamber by the microprocessor system, based on the received amplified electrical signal.

According to the above-mentioned method, prior to the step c, the method further comprises a step in which the infrared light pulse passes through a band pass filter having a central wavelength as the specific wavelength $\lambda$; and the processing process in the step c comprises the steps of:

c1: converting the infrared light pulse signal which has passed through the detecting chamber into an electrical signal;

c2: amplifying the electrical signal and then sending the amplified electrical signal to a microprocessor system; and c3. computing a measured value $C_0$ of the concentration of the gas to be detected in the detecting chamber by the microprocessor system, based on the received amplified electrical signal.

According to the above-mentioned method, the infrared light is converted into the infrared light pulse in such a manner that the infrared light passes through a light chopper which is rotated at a certain speed rate by a drive motor.

According to the above-mentioned method, said calibration step is started automatically and periodically, or started manually, so as to update the calibration factor $\beta$.

According to the above-mentioned method, the reference gas is the same kind as the gas to be detected.

According to the above-mentioned method, the gas to be detected is $CO_2$ in a breathing gas of human body.

According to the above-mentioned method, the known concentration value $C_1$ of the reference gas in the reference chamber is selected to be equal or close to a medium value of a concentration range of the gas to be detected.

In other aspect of the present invention, there is an apparatus for detecting gas concentration with infrared absorption characteristics, in which a gas to be detected having maximum absorption to an infrared light at a specific wavelength $\lambda$, the apparatus comprising:

a detecting light path unit which includes: an infrared light source for emitting the infrared light containing the specific wavelength $\lambda$; and a detecting chamber being located in the detecting light path and containing the gas to be detected, wherein the infrared light passes through the detecting chamber, and thereby forms an infrared light signal reflecting concentration information of the gas to be detected;

a gas path unit for feeding gas containing a certain amount of the gas to be detected into the detecting chamber; and a processing unit for processing the infrared light signal to obtain the calibrated concentration of the gas to be detected;

wherein the detecting light path unit further includes a reference chamber for a calibration process in which a reference gas having a known concentration $C_1$ is filled hermetically; and the apparatus further comprises a chamber switching device, which is used for switching the reference chamber into the detecting light path of the detecting light path unit during the calibration process and for switching the detecting chamber into the detecting light path of the detecting light path unit during the detection process.

According to the above-mentioned apparatus, the chamber switching unit comprises:

a frame, on which the reference chamber and the detecting chamber are mounted side by side; and a first eletromagnetic switch and a second eletromagnetic switch, which are positioned on the frame and connected to either side of the reference chamber and the detecting chamber respectively;

wherein during the detection process, the detecting chamber is positioned in the detecting light path by the first eletromagnetic switch and the second eletromagnetic switch; and during the calibration process, the reference chamber is positioned in the detecting light path by the first eletromagnetic switch and the second eletromagnetic switch.

According to the above-mentioned apparatus, the frame is a concave casing having a rail at an inner bottom thereof; the reference chamber and the detecting chamber are mounted on the rail of the concave casing side by side; the first eletromagnetic switch and the second eletromagnetic switch are arranged at two inner sidewalls of the concave casing respectively; a spring is arranged between the detecting chamber and the second eletromagnetic switch; the reference chamber is moved rightwards and switched into the detecting light path when the first eletromagnetic switch is turned off and the second eletromagnetic switch is turned on.

According to the above-mentioned apparatus, the apparatus further comprises a pulse generator for converting the infrared light into an infrared light pulse signal; and the pulse generator includes: a drive motor, and a light chopper for allowing the infrared light to pass through and rotated at stable speed rate by the drive motor.

According to the above-mentioned apparatus, the processing unit comprises:

an infrared sensor for converting the infrared light pulse signal which has passed through the detecting chamber into an electrical signal;

an amplification circuit for amplifying the electrical signal with a selected frequency; and a microprocessor system for computing the concentration of the gas to be detected according to the electrical signal.

According to the above-mentioned apparatus, signal output ports of the microprocessor system are connected with a drive motor control circuit which is connected to the drive motor and a chamber switching control circuit which is connected to the electromagnetic switches of the chamber switching unit.

According to the above-mentioned apparatus, a control panel of the apparatus is provided with a manual operation button which is connected to the chamber switching control circuit, so that an instruction for switching the reference chamber can be sent out via the manual operation button by the user according to the operation situation of the apparatus if necessary, and thereby the calibration process is started to update the calibration factor.

According to the above-mentioned apparatus, the gas path unit comprises a sampling gas path connected to an inlet of the detecting chamber, an orifice restrictor and a gas bump which are connected to the outlet of the detecting chamber, and the gas path unit is used for feeding the gas to be detected into the detecting chamber and discharging it after completion of the detection process.

According to the above-mentioned apparatus, signal output ports of the microprocessor system are connected with a flow rate detecting circuit connected to the orifice restrictor and a gas bump control circuit connected to the gas bump.

According to the above-mentioned apparatus, the detecting light path unit further comprises a light filter which is positioned in front of an infrared light inlet of the detecting chamber or behind an infrared light outlet of the detecting chamber.

Compared with the prior art, the method and the apparatus for detecting gas concentration with infrared absorption characteristics according to the present invention have the advantages as follows:

1. In the present invention, the same detecting light path (e.g. the infrared light source, and the light filter, etc.), the same infrared light signal processing unit (e.g. the infrared sensor, the amplification circuit and the single-chip microcomputer system, etc.) are used for both the calibration process and the detection process. Therefore, the negative effect caused by difference of the characteristics of temperature drift of circuit components between different light paths in prior art can be eliminated, and the errors in the detected results by using the apparatus in the present invention is greatly reduced.

2. Only one set of light path unit is required for the apparatus in the present invention. Therefore the structure of the apparatus is simple and the producing cost is reduced.

3. The calibration can be automatically performed after a certain period without any manual work. Therefore, the maintenance cost for the apparatus in the present invention is greatly reduced.

DETAILED DESCRIPTION OF PREFERRED EMBODIMENTS

Figure 1:
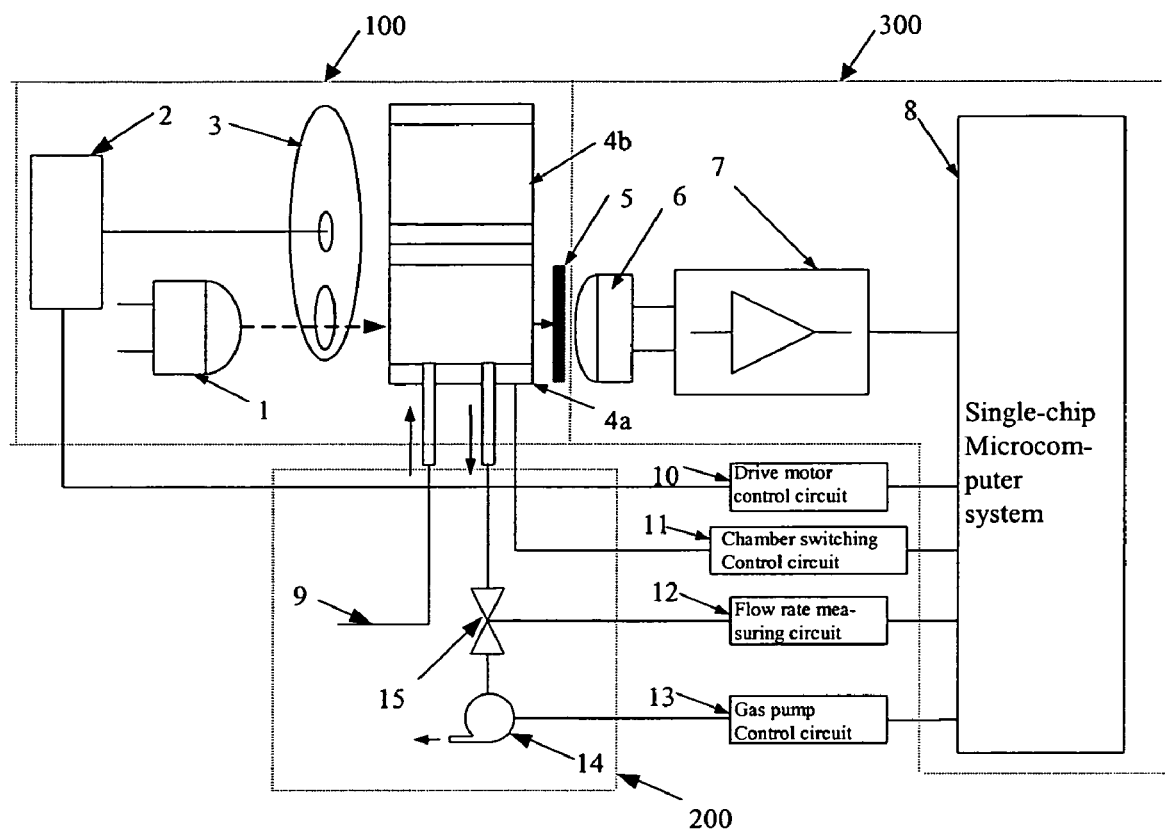
FIG. 1 is a block diagram illustrating the principle of an apparatus for detecting gas concentration with infrared absorption characteristics according to the present invention.

In one aspect of the present invention, there is an apparatus for detecting gas concentration with infrared absorption characteristics, in which a gas to be detected having maximum absorption to an infrared light at a specific wavelength $\lambda$, the apparatus comprising:

a detecting light path unit 100 which includes: an infrared light source 1 for emitting the infrared light containing the specific wavelength $\lambda$; and a detecting chamber 4a being located in the detecting light path and containing the gas to be detected, wherein the infrared light passes through the detecting chamber 4a, and thereby forms an infrared light signal reflecting concentration information of the gas to be detected;

a gas path unit 200 for feeding gas containing a certain amount of the gas to be detected into the detecting chamber 4a; and a processing unit 300 for processing the infrared light signal to obtain the calibrated concentration of the gas to be detected;

wherein the detecting light path unit 100 further includes a reference chamber 4b for a calibration process in which a reference gas having a known concentration $C_1$ is filled hermetically; and the apparatus further comprises a chamber switching device, which is used for switching the reference chamber 4b into the detecting light path of the detecting light path unit during the calibration process and for switching the detecting chamber 4a into the detecting light path of the detecting light path unit during the detection process.

In another aspect of the present invention, there is a method for detecting gas concentration with infrared absorption characteristics, comprising the following steps:

a. feeding gas containing a certain amount of gas to be detected into a detecting chamber 4a in a detecting light path,;

b. transmitting an infrared light containing a specific wavelength $\lambda$ through the detecting chamber 4a, so as to generate an infrared light signal reflecting concentration information of the gas to be detected, wherein the gas to be detected has maximum absorption to the infrared light at the specific wavelength $\lambda$;

c. processing the infrared light signal which passed through the detecting chamber 4a, so as to obtain a measured value $C_0$ of the concentration of the gas to be detected; and d. computing a calibrated value C of the concentration of the gas to be detected according to a formula $C=C_0*\beta$, wherein $\beta$ is a calibration factor;

wherein the calibration factor $\beta$ is obtained by a calibration step of:

switching a reference chamber 4b filled with a reference gas having a known concentration value $C_1$ into the detecting light path to replace the detecting chamber 4a, then repeating the step b and the step c to obtain a measured value $C_2$ of the concentration of the reference gas in the reference chamber 4b, and thus determining the calibration factor $\beta$ by a formula of $\beta=C_1/C_2$ according to the measured value $C_2$ and the known concentration value $C_1$ of the reference gas.

The apparatus and method of the present invention will be further described as follows in connection with the corresponding drawings, in which the most preferable embodiment of the present invention is illustrated.

As shown in FIG. 1, according to the present invention, the apparatus for detecting gas concentration with infrared absorption characteristics comprises:

a detecting light path unit 100 comprising an infrared light pulse generator, a detecting chamber 4a, a light filter 5 arranged sequentially, wherein the infrared light pulse generator comprises an infrared light source 1, a drive motor 2 and a light chopper 3, the drive motor 2 being connected to a single-chip microcomputer system 8 via a drive motor control circuit 10, and the light chopper 3 being driven to rotate at stable speed rate by the drive motor 2 under the control of the single-chip microcomputer system 8, so that an infrared light pulse is generated after the infrared light emitted by the infrared light source 1 passes through the light chopper 3;

a gas path unit 200 for feeding a certain amount of gas to be detected into the detecting chamber 4a and then discharging it to the atmosphere after the completion of detection process, the gas path unit comprising a sampling gas path 9 which is connected to an inlet of the detecting chamber 4a, an orifice restrictor 15 which is connected to an outlet of the detecting chamber 4a, and a gas bump 14, wherein the orifice restrictor 15 and the gas bump 14 are connected to the single-chip microcomputer system 8 via a flow rate measuring circuit 12 and a gas bump control circuit 13 correspondingly; and a processing unit 300 for processing the infrared light signal to obtain the calibrated concentration of the gas to be detected; the processing unit comprises: an infrared sensor for converting the infrared light pulse signal which has passed through the detecting chamber into an electrical signal; an amplification circuit for amplifying the electrical signal with a selected frequency; and a microprocessor system, which may be a single-chip microcomputer system storing computer program and control program, for computing the concentration of the gas to be detected according to the electrical signal. The microprocessor system drives the motor and controls the chamber switching through the respective control circuit. These control circuits connected to output ports of the single-chip microcomputer system 8 comprise the drive motor control circuit 10, a chamber switching control circuit 11, the flow rate measuring circuit 12, and the gas bump control circuit 13.

The apparatus of the present invention is distinguished from that of the prior art lies in that the detecting light path unit further comprises a reference chamber 4b which is filled with a gas having the known concentration in advance. The reference chamber 4b and the detecting chamber 4a are mounted in one chamber switching unit which is connected to the single-chip microcomputer system 8 via the chamber switching control circuit 11. Either of the reference chamber 4b and the detecting chamber 4a can be switched into the detecting light path of the detecting light path unit under the control of single-chip microcomputer system 8, so that the calibration factor β, which reflects an observation error from an instrument component and a computational error, can be computed and used to calibrate the detected result of gas concentration. The calibration factor β may be computed in every concentration detection process. The calibration factor β may be kept constant in a period which is preset by system program in view that the variation of it is quite small in this period. The reference chamber 4b will be switched periodically, such as every one month, into the detecting light path under the control of single-chip microcomputer system 8 according to the period preset by system program, so as to compute the calibration factor.

Figure 2:
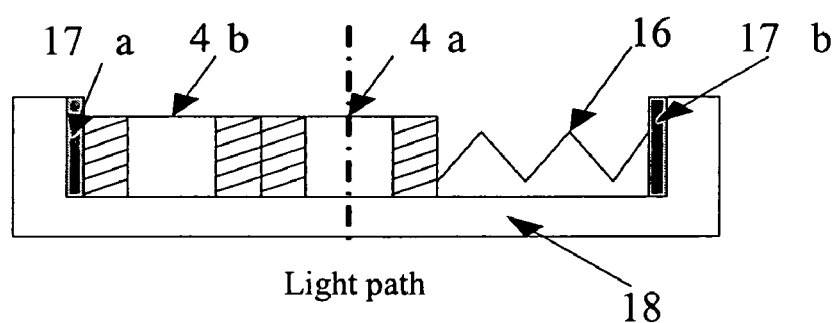
FIG. 2 is a schematic diagram for illustrating the structure that a reference chamber and a detecting chamber of the detecting light path unit in FIG. 1 are mounted in one chamber switching unit.

The chamber switching unit comprises: a frame, which may be a concave casing 18 having a rail at an inner bottom thereof, so that the reference chamber 4b and the detecting chamber 4a are mounted to the rail in the concave casing 18 side by side; and a first eletromagnetic switch 17a and a second eletromagnetic switch 17b which are controlled by the single-chip microcomputer system 8. The first eletromagnetic switch 17a and the second eletromagnetic switch 17b are arranged at two inner sidewalls of concave casing 18, respectively. A spring 16 is arranged between the detecting chamber 4a and the second eletromagnetic switch 17b. As shown in FIG. 2, under normal condition (i.e. in the detection process), the detecting chamber 4a is positioned in the detecting light path. The reference chamber 4b is switched and moved right into the detecting light path when the first eletromagnetic switch 17a is turned off and the second eletromagnetic switch 17b is turned on under the control of the single-chip microcomputer system 8, so as to perform the calibration.

The control panel of the apparatus is provided with a manual operation button which is connected to the chamber switching control circuit 11. An instruction for switching the reference chamber 4b can be sent out via the manual operation button by the user according to the operation situation of the apparatus if necessary, so that the calibration process is started to update the calibration factor in the apparatus of the present invention.

A method used in the above apparatus for detecting gas concentration with infrared absorption characteristics, comprises the following steps:

a. feeding gas containing a certain amount of a gas to be detected into the detecting chamber 4a via the sampling gas path 9, the gas to be detected having maximum absorption to an infrared light of the wavelength $\lambda$;

b. driving the light chopper 3 to rotate at stable speed rate by the drive motor 2 under the control of the single-chip microcomputer system 8, so that an infrared light pulse is generated after the infrared light emitted from the infrared light source 1 passes through the light chopper 3, and an infrared light pulse signal reflecting concentration information of the gas to be detected is then generated after the infrared light pulse passes through the detecting chamber 4a;

c. passing the infrared light pulse signal through a band pass filter 5 with a central wavelength $\lambda$, and then converting the light pulse signal into an electrical signal by an infrared sensor 6; wherein the gas to be detected is, for example, $CO_2$ in a breathing gas of human being, the wavelength $\lambda$ of which is 4.26 micrometer.

d. amplifying the electrical signal by the amplification circuit 7 and then sending the amplified/electrical signal to the single-chip microcomputer system 8;

e. based on the received amplified electrical signal, computing a measured value $C_0$ of concentration of the gas to be detected in the detecting chamber 4a by the single-chip microcomputer system 8, wherein the computed concentration value $C_0$ must be calibrated because it includes an observation error from instrument components and a computational error;

f. computing a calibrated value C of the concentration of the gas to be detected according to a formula of $C=C_0*\beta$, where $\beta$ is a calibration factor, C is the final result for the gas concentration to be detected;

wherein the method of the present invention is distinguished from prior art in that the calibration factor $\beta$ is obtained by the following calibration step:

switching a reference chamber filled with a reference gas having a known concentration value $C_1$ into the detecting light path to replace the detecting chamber, then repeating the step b to the step e to obtain a measured value $C_2$ of the concentration of the reference gas in the reference chamber, and thus determining the calibration factor $\beta$ by a formula of $\beta=C_1/C_2$ according to the measured value $C_2$ and the known concentration value $C_1$ of the reference gas; wherein the calibration factor $\beta$ represents the deviation extent of the detected gas concentration $C_2$ with respect to the known gas concentration $C_1$.

The calibration factor $\beta$ can be computed in real-time during each detection process. Alternatively, the calibration factor $\beta$ can be also stored in EEPROM (Electrically Erasable Programmable Read Only Memory) of the single-chip microcomputer system 8 so as to be repeatedly used for a certain period, and the step g will be periodically and automatically started to update the calibration factor $\beta$ by the apparatus.

In addition, the control panel of the apparatus is provided with a manual operation button by which the step g can be manually started to update the calibration factor $\beta$ by the user according to the operation situation of the apparatus.

The known concentration $C_1$ of the gas in the reference chamber 4b is selected to be equal or close to the medium value of a concentration range of the gas to be detected. For some kinds of gas whose concentration may in a wide range, the calibration factor $\beta$ may be related to the selection of C1. Therefore, in this case, it is preferred that the known concentration $C_1$ is selected to be the medium value of the wide range of the concentration.

In view that different gas has different light absorption characteristics, the concentration of any gas which has infrared absorption characteristics can be detected and automatically calibrated by the method and the apparatus of the present invention as long as the wavelength of the light source, the sensor, and the type of the gas in the reference chamber are changed correspondingly.

As an example, an apparatus, which is widely used in medical treatment to detect the concentration of $CO_2$ in breathing gas of the human being, can employ the technical solution of the present invention. Since $CO_2$ gas has maximum absorption to the infrared light with the wavelength of 4.26 micrometer, the light source and the sensor should be capable of generating the infrared light with the wavelength of 4.26 micrometer and separating it. Accordingly, the filled gas in the reference chamber is $CO_2$ gas.

The operation principle of the apparatus for detecting the concentration of $CO_2$ in breathing gas of the human being with automatic calibration function will be described as follows.

The light chopper 3 is rotated at a certain speed rate by the drive motor 2, and then an infrared light pulse signal is generated after the infrared light emitted from the infrared light source 1 passes through the hole of the light chopper 3. While the infrared light pulse signal passes through the detecting chamber 4a filled with $CO_2$ gas, the infrared light which wavelength is about 4.26 micrometer will be absorbed by $CO_2$ gas so that the energy of the infrared light which reaches the infrared sensor 6 changes with the variation of the concentration of $CO_2$ in the detecting chamber 4a. The infrared light, which has passed through the detecting chamber 4a and the band pass filter 5 with a central wavelength of 4.26 micrometer, is converted into the corresponding electrical signal by the infrared sensor 6, and then input into the single-chip microcomputer system 8 for subsequent processing. A certain amount of sample gas from the breathing gas of a patient is continuously pumped into the detecting chamber 4a by the gas pump 14 via the sampling gas path 9, and discharged from an outlet of the detecting chamber 4a to the atmosphere after the detection process. The pumping speed of gas can be measured in real-time by the flow rate detecting control circuit 12 and the pumping speed of gas pump 14 can be adjusted by the gas pump control circuit 13 under the control of the single-chip microcomputer system 8, so as to keep the pumping speed stable during the gas sampling process.

A portion of the infrared light emitted from the infrared light source 1 would be absorbed by $CO_2$ while passing through the gas to be detected. Accordingly, light intensity received by the infrared light sensor will vary, which meets Beer-Lambert law:

$$I = I_0 \cdot e^{-aLC}$$

where, I is the intensity of the infrared light before absorption, $I_0$ the intensity of the infrared light after absorption, a is the absorption coefficient of $CO_2$ gas for an infrared light with the wavelength of 4.26 micrometer, L is the effective absorption optical length of the gas to be detected, and C is the concentration of the gas to be detected. Since $I_0$, a, and L are kept constant in the apparatus, the concentration of $CO_2$ to be detected can be determined by means of the ready-made intensity-concentration plot, i.e. the relationship between the attenuated intensity of the infrared light and the concentration of $CO_2$ gas, according to the attenuated intensity of the infrared light. However, since the light source, the sensor and the amplification circuit of different apparatuses have difference, the intensity-concentration plot of different apparatuses will be different from the ready-made one. In general, this kind of difference can be eliminated by the calibration process. That is, $CO_2$ gas having the known concentration of $C_1$ is input into the apparatus, the detected concentration of $CO_2$ is $C_2$, then the calibration factor $\beta$ is determined by a formula $\beta = C_1/C_2$. Therefore, the final result of detected concentration is $C*\beta$ after the calibration process.

Under normal detecting condition, the detecting chamber 4a is positioned in the detecting light path; the infrared sensor 6 can sense the attenuated light intensity of the infrared light which has passed the gas to be detected in the detecting chamber 4a. $CO_2$ gas having a predetermined concentration, for example 5%, is sealed in the reference chamber 4b. If the calibration process is needed, the first eletromagnetic switch 17a is turned off and the second eletromagnetic switch 17b is turned on under the control of the single-chip microcomputer system 8, so that the reference chamber 4b is switched into the detecting light path, and thereby the infrared sensor 6 can sense the attenuated light intensity of the infrared light having passed $CO_2$ gas with known predetermined concentration in the reference chamber 4b. Based on the detected results during the calibration, the calibration factor $\beta$ is automatically computed by the single-chip microcomputer system 8 and stored in EEPROM of the single-chip microcomputer system 8. When the calibration process is completed, the electromagnetic switches are controlled by the single-chip microcomputer system 8 so that the detecting chamber 4a is switched to return in the detecting light path. The size of the reference chamber 4b and the material of the hermetical window thereof are the same as those of the detecting chamber 4a.

It can be understood by the technicians in this art:

1) in the preferred embodiments of the detection method and apparatus according to the present invention, the infrared light transmitted into the gas chamber is of pulse; accordingly, the infrared sensor is one be capable of receiving the AC signal. However, the infrared light transmitted into the gas chamber may not be of pulse form; accordingly, the infrared sensor is one be capable of receiving the DC signal.

2) in addition, in the case that the infrared light source has good monochromaticity, the light filter is not required. When using the light filter, the light filter is not limited to be behind an infrared light outlet of the detecting chamber, it may also be in front of an infrared light inlet of the detecting chamber.

3) in the calibration process, it is preferred that the reference gas is the same kind as the gas to be detected.

What is claimed is:

1. A method for detecting gas concentration with infrared absorption characteristics, comprising the following steps:
   a. feeding gas containing a certain amount of gas to be detected into a detecting chamber in a detecting light path;
   b. transmitting an infrared light containing a specific wavelength $\lambda$ through the detecting chamber, so as to generate an infrared light signal reflecting concentration information of the gas to be detected, wherein the gas to be detected has maximum absorption to the infrared light at the specific wavelength $\lambda$;
   c. processing the infrared light signal which passed through the detecting chamber, so as to obtain a measured value $C_0$ of the concentration of the gas to be detected; and
   d. computing a calibrated value C of the concentration of the gas to be detected according to a formula $C = C_0 * \beta$, wherein $\beta$ is a calibration factor;
   wherein the calibration factor $\beta$ is obtained by a calibration step of:
   switching a reference chamber filled with a reference gas having a known concentration value $C_1$ into the detecting light path to replace the detecting chamber, then repeating the step b and the step c to obtain a measured value $C_2$ of the concentration of the reference gas in the reference chamber, and thus determining the calibration factor $\beta$ by a formula of $\beta=C_1/C_2$ according to the measured value $C_2$ and the known concentration value $C_1$ of the reference gas.

2. The method according to claim 1, wherein the step b further comprises a step of converting the infrared light into an infrared light pulse, wherein the infrared light pulse passes through the detecting chamber, and thereby forms an infrared light pulse signal reflecting concentration information of the gas to be detected.

3. The method according to claim 2, wherein said processing in the step c comprises the steps of:
   c1: transmitting the infrared light pulse signal which has passed through the detecting chamber into a band pass filter having a central wavelength as the specific wavelength $\lambda$, and then converting the infrared light pulse signal which has passed through the band pass filter into an electrical signal;
   c2: amplifying the electrical signal and then sending the amplified electrical signal to a microcomputer system; and
   c3. computing a measured value $C_0$ of the concentration of the gas to be detected in the detecting chamber by the microprocessor system, based on the received amplified electrical signal.

4. The method according to claim 2, wherein prior to the step c, the method further comprises a step in which the infrared light pulse passes through a band pass filter having a central wavelength as the specific wavelength $\lambda$; and
   said processing in the step c comprises the steps of:
   c1: converting the infrared light pulse signal which has passed through the detecting chamber into an electrical signal;
   c2: amplifying the electrical signal and then sending the amplified electrical signal to a microprocessor system; and
   c3. computing a measured value $C_0$ of the concentration of the gas to be detected in the detecting chamber by the microprocessor system, based on the received amplified electrical signal.

5. The method according to claim 2, wherein the infrared light is converted into the infrared light pulse in such a manner that the infrared light passes through a light chopper which is rotated at a certain speed rate by a drive motor.

6. The method according to claim 1, wherein said calibration step is started automatically and periodically, or started manually, so as to update the calibration factor $\beta$.

7. The method according to claim 1, wherein the reference gas is the same kind as the gas to be detected.

8. The method according to claim 1, wherein the gas to be detected is $CO_2$ in a breathing gas of human body.

9. The method according to claim 1, wherein the known concentration value C1 of the reference gas in the reference chamber is selected to be equal to or substantially equal to a mean value of a concentration range of the gas to be detected.

10. An apparatus for detecting gas concentration with infrared absorption characteristics, in which a gas to be detected having maximum absorption to an infrared light of a specific wavelength $\lambda$, the apparatus comprising:
   a detecting light path unit which includes: an infrared light source for emitting the infrared light containing the specific wavelength $\lambda$; and a detecting chamber being located in the detecting light path and containing the gas to be detected, wherein the infrared light passes through the detecting chamber, and thereby forms an infrared light signal reflecting concentration information of the gas to be detected;
   a gas path unit for feeding gas containing a certain amount of the gas to be detected into the detecting chamber; and
   a processing unit for processing the infrared light signal to obtain the calibrated concentration of the gas to be detected;
   wherein the detecting light path unit further includes a reference chamber for a calibration process in which a reference gas having a known concentration $C_1$ is filled hermetically; and
   the apparatus further comprises a chamber switching device, which is used for switching the reference chamber into the detecting light path of the detecting light path unit during the calibration process and for switching the detecting chamber into the detecting light path of the detecting light path unit during the detection process.

11. The apparatus according to claim 10, wherein the apparatus further comprises a pulse generator for converting the infrared light into an infrared light pulse signal; and the pulse generator includes: a drive motor, and a light chopper for allowing the infrared light to pass through and rotated at stable speed rate by the drive motor.

12. The apparatus according to claim 11, wherein the processing unit comprises:
   an infrared sensor for converting the infrared light pulse signal which has passed through the detecting chamber into an electrical signal;
   an amplification circuit for amplifying the electrical signal with a selected frequency; and
   a microprocessor system which stores computer program and control program, for computing the concentration of the gas to be detected according to the electrical signal.

13. The apparatus according to claim 12, wherein signal output ports of the microprocessor system are connected with a drive motor control circuit which is connected to the drive motor and a chamber switching control circuit which is connected to the electromagnetic switches of the chamber switching unit.

14. The apparatus according to claim 13, wherein a control panel of the apparatus is provided with a manual operation button which is connected to the chamber switching control circuit, so that an instruction for switching the reference chamber can be sent out via the manual operation button by the user according to the operation situation of the apparatus if necessary, and thereby the calibration process is started to update the calibration factor.

15. The apparatus according to claim 12, wherein the gas path unit comprises a sampling gas path connected to an inlet of the detecting chamber, an orifice restrictor and a gas bump connected to an outlet of the detecting chamber; and the gas path unit is used for feeding the gas to be detected into the detecting chamber and discharging it after completion of the detection process.

16. The apparatus according to claim 15, wherein signal output ports of the microprocessor system are connected with a flow rate detecting circuit connected to the orifice restrictor and a gas bump control circuit connected to the gas bump.

17. The apparatus according to claim 10, wherein the chamber switching unit comprises:
   a frame, on which the reference chamber and the detecting chamber are mounted side by side; and a first electromagnetic switch and a second electromagnetic switch, which are positioned on the frame and connected to either side of the reference chamber and the detecting chamber respectively;

wherein during the detection process, the detecting chamber is positioned in the detecting light path by the first electromagnetic switch and the second electromagnetic switch; and during the calibration process, the reference chamber is positioned in the detecting light path by the first electromagnetic switch and the second electromagnetic switch.

18. The apparatus according to claim 17, wherein the frame is a concave casing having a rail at an inner bottom thereof; the reference chamber and the detecting chamber are mounted on the rail of the concave casing side by side; the first electromagnetic switch and the second electromagnetic switch are arranged at two inner sidewalls of the concave casing respectively; a spring is arranged between the detecting chamber and the second electromagnetic switch; the reference chamber is moved rightwards and switched into the detecting light path when the first electromagnetic switch is turned off and the second electromagnetic switch is turned on.

19. The apparatus according to claim 10, wherein the detecting light path unit further comprises a light filter which is positioned in front of an infrared light inlet of the detecting chamber or behind an infrared light outlet of the detecting chamber.

* * * * *